United States Patent
Mashak

(10) Patent No.: US 7,207,331 B2
(45) Date of Patent: Apr. 24, 2007

(54) ARRANGEMENT AND METHOD FOR CONTROLLING OPERATIONAL CHARACTERISTICS OF MEDICAL EQUIPMENT

(75) Inventor: James N. Mashak, Sun Prairie, WI (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/086,025

(22) Filed: Mar. 22, 2005

(65) Prior Publication Data

US 2006/0213517 A1 Sep. 28, 2006

(51) Int. Cl.
- *A61M 16/00* (2006.01)
- *A62B 7/00* (2006.01)
- *F16K 31/02* (2006.01)

(52) U.S. Cl. .................. 128/204.21; 128/200.24; 128/204.18; 128/204.23

(58) Field of Classification Search ........... 128/204.21, 128/204.22, 204.23, 204.29, 204.18, 202.22, 128/205.23, 202.28, 202.29, 203.11, 200.24; 345/156

See application file for complete search history.

(56) References Cited

U.S. PATENT DOCUMENTS

| | | | |
|---|---|---|---|
| 3,256,876 A * | 6/1966 | Elam ................. | 128/205.15 |
| 3,874,378 A * | 4/1975 | Isaacson et al. ....... | 128/205.24 |
| 3,890,967 A * | 6/1975 | Elam et al. .......... | 128/205.17 |
| 4,187,845 A * | 2/1980 | Dror ................. | 128/205.13 |
| 4,407,393 A * | 10/1983 | Youdin et al. ........ | 188/2 F |
| 4,865,610 A * | 9/1989 | Muller ............... | 623/24 |
| 4,991,576 A * | 2/1991 | Henkin et al. ........ | 128/203.28 |
| 5,019,056 A * | 5/1991 | Lee et al. ........... | 604/257 |
| 5,103,807 A * | 4/1992 | Makaran ............. | 601/40 |
| 5,231,981 A * | 8/1993 | Schreiber et al. ..... | 128/205.23 |
| 5,365,026 A * | 11/1994 | Cromer et al. ....... | 200/1 R |
| 5,507,280 A * | 4/1996 | Henkin et al. ........ | 128/203.12 |
| 5,537,999 A * | 7/1996 | Dearman et al. ...... | 128/205.25 |
| 5,551,419 A * | 9/1996 | Froehlich et al. ..... | 128/204.23 |
| 5,564,416 A * | 10/1996 | Jones ................ | 128/204.21 |
| 5,628,305 A * | 5/1997 | Melker ............... | 128/202.29 |
| 5,651,361 A * | 7/1997 | Dearman et al. ...... | 128/205.25 |
| 5,678,537 A | 10/1997 | Bathe et al. | |
| 5,694,924 A * | 12/1997 | Cewers ............... | 128/204.21 |
| 5,711,295 A * | 1/1998 | Harris, II ............ | 128/202.28 |
| 5,867,821 A * | 2/1999 | Ballantyne et al. .... | 705/2 |
| 5,868,133 A * | 2/1999 | DeVries et al. ....... | 128/204.21 |

(Continued)

Primary Examiner—Patricia Bianco
Assistant Examiner—Nihir Patel
(74) Attorney, Agent, or Firm—Andrus, Sceales, Starke & Sawall, LLP

(57) ABSTRACT

An arrangement and method is provided for controlling operational characteristics of medical equipment. A pressure sensor associated with the caregiver is arranged to sense changes in air pressure that correspond to breathing activity of the caregiver. The pressure sensor may comprise a neckband, headset, or the like. In the arrangement shown, a headset that is worn by the caregiver includes a disposable tube connected to a pressure transducer such that the pressure sensor senses changes in air pressure in the tube. An open end of the tube is positioned near the mouth of the caregiver to receive changes in airflow from the caregiver's mouth. The pressure sensor is in communication with a controller associated with the ventilator. The controller is arranged to control at least one operational parameter of the ventilator, such as the delivery of respiratory support to the patient or actuation of an oxygen flush valve on the ventilator, based upon the changes in air pressure sensed by the pressure sensor.

7 Claims, 3 Drawing Sheets

U.S. PATENT DOCUMENTS

| | | | |
|---|---|---|---|
| 5,961,561 A * | 10/1999 | Wakefield, II | 701/29 |
| 5,975,078 A * | 11/1999 | Pauley | 128/205.23 |
| 6,036,662 A * | 3/2000 | Van Brunt et al. | 601/41 |
| 6,082,583 A * | 7/2000 | Bussell et al. | 222/1 |
| 6,459,933 B1 * | 10/2002 | Lurie et al. | 607/5 |
| 6,481,688 B1 * | 11/2002 | Welling et al. | 248/694 |
| 6,705,316 B2 * | 3/2004 | Blythe et al. | 128/204.18 |
| 6,761,344 B2 * | 7/2004 | Welling et al. | 248/694 |
| 6,801,231 B1 * | 10/2004 | Beltz | 715/865 |
| 6,833,786 B1 | 12/2004 | Sun et al. | |
| 6,834,647 B2 * | 12/2004 | Blair et al. | 128/204.18 |
| 6,840,240 B1 * | 1/2005 | Berthon-Jones et al. | 128/204.21 |
| 6,876,303 B2 * | 4/2005 | Reeder et al. | 340/573.1 |
| 6,880,556 B2 * | 4/2005 | Uchiyama et al. | 128/205.24 |
| 2003/0050794 A1 * | 3/2003 | Keck | 705/2 |
| 2005/0022815 A1 * | 2/2005 | Frola | 128/204.21 |
| 2005/0066969 A1 * | 3/2005 | Rick et al. | 128/204.18 |
| 2005/0076906 A1 * | 4/2005 | Johnson | 128/204.21 |

* cited by examiner

ARRANGEMENT AND METHOD FOR CONTROLLING OPERATIONAL CHARACTERISTICS OF MEDICAL EQUIPMENT

FIELD OF THE INVENTION

The present invention relates to an arrangement and method for controlling operational characteristics of medical equipment. In the particular embodiment shown and described hereinbelow, an arrangement and method for controlling an anesthesia machine based upon breathing activity of an operator/caregiver is provided. It will be recognized by those skilled in the art that the present invention is also applicable to a wide variety of other medical equipment.

BACKGROUND OF THE INVENTION

In general, anesthesia systems comprise various equipment necessary to anesthetize a patient and maintain the patient in an anesthetized state until a particular medical procedure is completed. Such systems typically include pressure regulators, flow control devices, gas mixing devices, and vaporizers to vaporize a volatile liquid anesthetic and to introduce the anesthetic laden gases into the patient. The patient is usually connected to the system by means of a facemask or other device. The facemask interfaces with the anesthesia system via a patient circuit that typically has an inspiratory limb through which the gases are introduced into the patient and an expiratory limb that conveys the exhaled gases from the patient. Such limbs may be separate conduits joined by a wye piece at or near the patient or may comprise coaxial conduits commonly known as Bain circuits.

In a typical anesthesia system, the overall flow of gases to and from the patient may be in a generally closed circuit. That is, the patient is connected to a substantially closed loop supply of gasses and re-breathes certain of those exhaled gases supplemented by fresh gas. Alternatively, the patient circuit could be an open circuit and all of the exhaled gases simply vented or channeled from the system to an external environment and not re-breathed by the patient. Other variety of circuits are used that deliver the anesthetic gases to the patient, such as semi-open circuits and the like.

As the driving force to the patient, a ventilator is used and which basically breathes for the patient since the patient is under anesthesia and is unable to carry out the normal spontaneous breathing functions. The ventilator, therefore, provides a quantity of the gas containing a metered quantity of the anesthetic agent along with other gases such as $N_2O$ and, of course, a life sustaining percentage of oxygen.

Gas containing the anesthetic may be delivered directly by the ventilator into the patient circuit for introduction to the patient or may include an intermediate mechanism such as a bellows. In the latter case, the gas from the ventilator does not contain the anesthetic agent but is used to simply power the bellows by collapsing the bellows to deliver the anesthetic containing gas from the bellows to the patient. With the use of a bellows, the patient is basically isolated from the ventilator and it is possible to use the bellows to allow re-breathing of the patient's exhaled gases to conserve those gases, including the anesthetic agent.

A patient can also be manually ventilated by means of a flexible container or "bag" provided on the ventilator. The bag is filled with breathing gases and manually squeezed by a clinician to provide breathing gases to the patient. Use of the bag or "bagging the patient" is often required or preferred by clinicians as it enables the clinician to physically control the delivery of breathing gases to the patient. Patients are often bagged during surgical procedures when anesthesia is induced in the patient by entraining the anesthetic in the breathing gases. Another environment in which patients are often bagged is in an intensive care unit.

Ventilators typically have two cycles, an inhalation cycle where gas is being forced into the patient and an exhalation cycle where the ventilator allows the patient to exhale through an exhalation valve that vents some of the exhaled gases from the system. The ventilator, therefore, controls both the patient's inhalation and exhalation and the overall circuit is fairly restricted with respect to gases from the overall system being vented to the surrounding ambient.

Another typical function of such anesthesia systems is an oxygen flush that is manually operated by the user to provide an instant flush of oxygen into the patient breathing circuit. The oxygen flush is commonly used to recharge the bellows in the case of a leak in the patient circuit or to rapidly purge the patient circuit of anesthetic gases in the event of an overdose of the anesthetic agent. The latter function is carried out whether or not there is a bellows being used in the anesthesia system and may be used where the anesthetic gases are supplied directly to the patient circuit from the ventilator. Generally, a manual valve is pushed by the user to activate the oxygen flush and the button, when released, stops the flush. When activated, the excess oxygen from the flush stream of oxygen is released by means of a popoff valve in the anesthetic circuit.

During manual ventilator or "bagging", the caregiver is often required to compress the bag with one or both hands, adjust pressure valves associated with the anesthesia system, press or turn a valve to operate the oxygen flush and keep the circuit full of gas, and in some cases hold a mask on the patient's face. These activities are time consuming and require the caregiver to devote both hands to the above-described manual operation. Also, if bagging is carried out for a long time, it becomes fatiguing to the caregiver, lessening both the fineness of the control of breathing gas supply and the sensing of lung or other respiratory conditions affecting the subject. The bag is usually positioned along the patient circuit, which restricts the degree to which the caregiver, when bagging a patient, can move about the patient, for example, to observe a surgical patient positioned in a manner appropriate to the surgery to be performed. The same is true when the pneumatic elements of the ventilator, rather than the bag, are providing the breathing gases to the patient since the controls necessary to operate the pneumatic elements are placed at a fixed location on the ventilator.

If a leak occurs in the breathing circuit, for example between the facemask and the patient, it is usually necessary to operate the oxygen flush to recharge the bellows, as described above. Such an event currently requires the caregiver to manually operate a flush valve or press and hold down a button on the ventilator to actuate the valve. This can be time consuming and typically requires the caregiver to interrupt other caregiving activity.

As such, it is desirable to provide a method and arrangement that enables a caregiver to control medical apparatus, such as an anesthesia machine and ventilator, without the need for direct manual interaction. Such an arrangement would allow the caregiver to perform other tasks during treatment of the patient.

SUMMARY OF THE INVENTION

The present invention relates to an arrangement and method for controlling operational characteristics of medical equipment in the healthcare environment. The arrangement and method advantageously provide a caregiver with the ability to control the medical equipment without the use of manual interaction, thus allowing the caregiver to move about the patient and medical equipment and pursue other manual tasks while simultaneously controlling the medical equipment.

The examples shown and depicted hereinbelow include an arrangement and method for controlling an anesthesia system based upon breathing activity of the caregiver. A pressure sensor associated with the caregiver is arranged to sense changes in air pressure that correspond to breathing activity of the caregiver. The pressure sensor may be part of a neckband, headset, or the like. In the arrangement shown, a headset that is worn by the caregiver carries a disposable tube that is pneumatically connected to a pressure transducer such that the pressure transducer senses changes in air pressure in the tube. An open end of the tube is positioned near the mouth of the caregiver to receive changes in airflow from the caregiver's mouth.

The pressure sensor is in communication with a controller associated with the ventilator. The controller is arranged to control at least one operational parameter of the ventilator, such as the delivery of respiratory support to the patient or actuation of the oxygen flush valve on the ventilator, based upon the changes in air pressure sensed by the pressure sensor.

According to one embodiment of the method of the invention, the pressure transducer senses the breathing activity of the caregiver via the tube, and the sensed breathing activity is communicated to the ventilator. An operational parameter of the ventilator is then controlled based upon the sensed breathing activity of the operator. For example, when the operator forcibly exhales, or "puffs" into the tube, the pressure transducer senses an increase in air pressure. Based upon the sensed increase in pressure, the controller controls the ventilator to initiate an inspiratory phase of respiratory support to the patient. When the caregiver forcibly inhales, or "sips" from the tube, the pressure transducer senses a decrease in pressure, which is then communicated to the ventilator. The ventilator is controlled to initiate an oxygen flush to recharge the patient breathing circuit with oxygen.

According to the system and method of the present invention, the caregiver is able to control the operation of the ventilator and to provide respiratory support to the patient without the need for manual control. Therefore, the caregiver advantageously has both hands available to perform other tasks. In addition, in one arrangement, the pressure sensor is coupled to the caregiver and wirelessly communicates the sensed breathing changes to the controller, such that the caregiver is free to move about and be distant from the patient and/or the ventilator.

The pressure sensor device may be arranged to control the operation characteristic of the medical apparatus based upon the duration and/or amount of pressure change detected by the pressure sensor. For example, a pressure transducer can be arranged to sense the volume of pressure change in the tube caused by a "puff" or "sip" from the caregiver. Based upon the amount of pressure change, the controller can provide a certain volume of flow of breathing gases to the patient, or a certain amount of oxygen from the oxygen flush. Similarly, the pressure transducer can be arranged to sense the duration of the "puff" or "sip" from the caregiver and provide breathing gases to the patient or oxygen from the oxygen flush for a corresponding duration.

In an additional example, the pressure sensor device includes an audio speaker, or earbud, that communicates information related to the medical equipment to the caregiver. The information can include, for example, ventilator settings, parameters or alarm information. This feature further enhances the ability of the caregiver to move about and be distant from the medical equipment and/or patient while simultaneously controlling the equipment.

Various other features, objects, and advantages of the invention will be made apparent from the following detailed description and drawings.

BRIEF DESCRIPTION OF THE DRAWINGS

The invention will be further understood from the following detailed description taken in conjunction with the drawings. In the drawings.

DETAILED DESCRIPTION OF THE PREFERRED EMBODIMENTS

Figure 1:
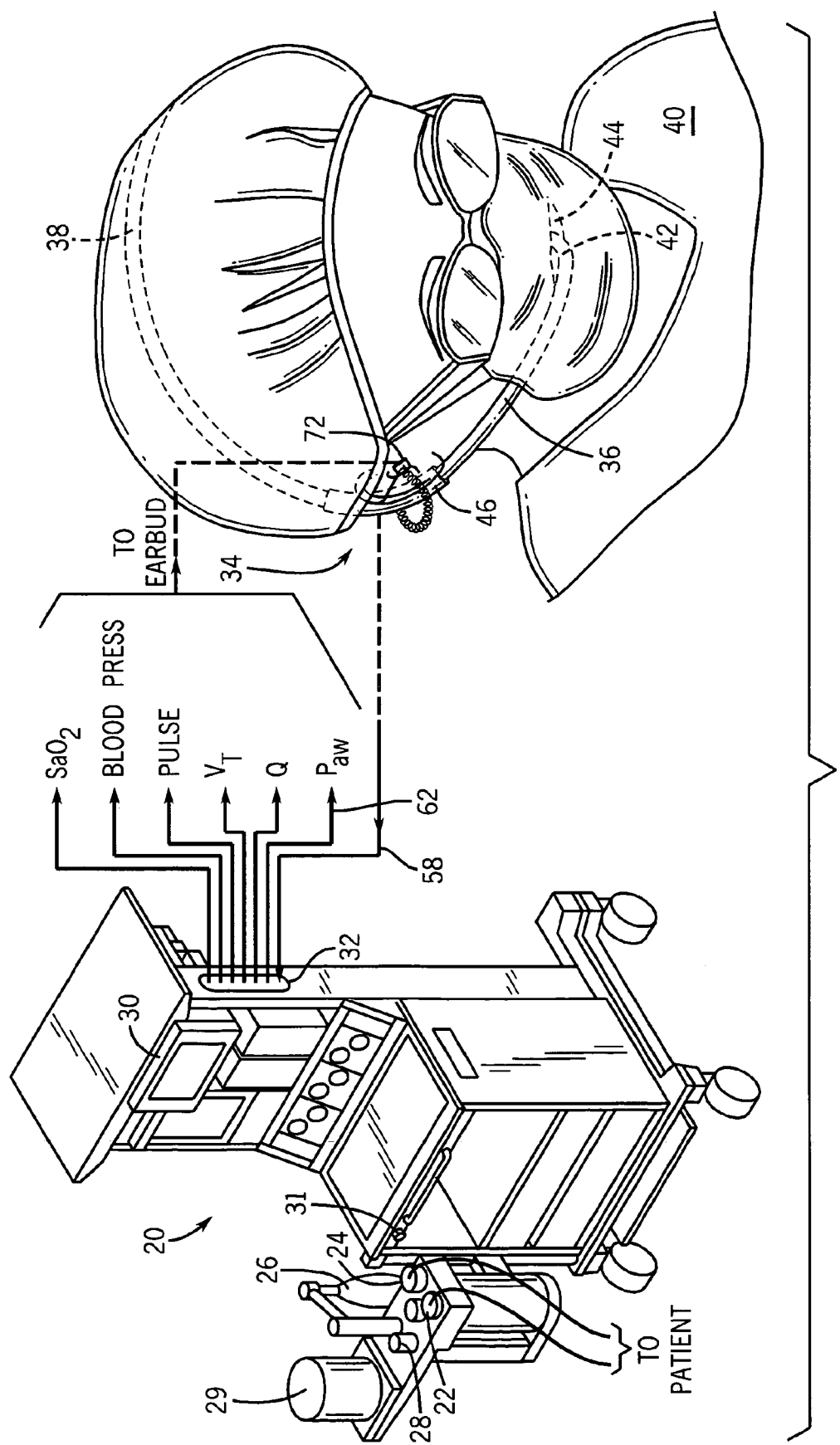
FIG. 1 shows a perspective view of an anesthesia machine and a pressure sensor device worn by the caregiver, wherein the pressure sensor device includes a pressure transducer that communicates with a controller associated with a ventilator apparatus in the anesthesia machine.

In the preferred embodiment of the present invention described in detail below, an arrangement and method for controlling operational characteristics of medical equipment is provided. It should be understood that the drawings and specification are to be considered an exemplification of the principles of the invention, which is more particularly defined in the appended claims. For example, although specific arrangements for an anesthesia machine and a pressure sensor device are depicted in the drawings, it should be recognized that the concepts of the present invention are applicable to a wide variety of medical apparatus and using a wide variety of pressure sensor devices.

Referring to FIG. 1, medical apparatus suitable for use with the present invention is shown as ventilator 20 incorporated in an anesthesia machine. Ventilator 20 has connections 22 and 24 suitable for connection to the inspiratory and expiratory limbs of a breathing circuit leading to the patient (the inspiratory and expiratory limbs are shown diagrammatically in FIG. 2 as 54 and 64, respectively). Ventilator 20 provides breathing gases to the patient via inspiratory limb 54 and receives gases expired by the patient via expiratory limb 64.

The breathing circuit is also provided with a bag 26 for manually bagging the patient. Switch 28 is manually operated to allow bag 26 to provide breathing gases to the patient. Ventilator 20 further includes a bellows 29. Gas from ventilator 20 is used to collapse the bellows 29 to deliver anesthetic containing gas from the bellows 29 to the patient. Ventilator 20 also includes an oxygen flush valve (shown schematically in FIG. 2 as 51) which is actuated by an actuator (shown illustratively in FIG. 1 as 31). When pressed, actuator 31 opens the flush valve 51 to provide a fresh supply of oxygen to the breathing circuit.

Ventilator 20 receives inputs from sensors associated with the patient and/or ventilator 20. The data contained in these inputs may be displayed on patient monitor 30. Data relating to the sensed parameters is also provided to terminal 32. Typical data outputs are shown as patient airway pressure $P_{aw}$, title volume $V_T$, breathing gas flow rate Q, pulse rate, blood pressure, and arterial blood oxygen saturation $SaO_2$ parameters.

FIG. 1 also depicts a pressure sensor device 34. Pressure sensor device 34 includes a tube 36 mounted on a headset 38 suitable to be worn by the operator/caregiver 40. Tube 36 is preferably formed of disposable plastic and is supported by the headset 38 such that its open end 42 is positioned near the mouth 44 of the operator/caregiver 40. In the example shown, tube 36 is oriented such that the caregiver 40 can close his or her lips around the open end 42 of the tube and form a seal. A closed end of the tube 36 is in pneumatic communication with a pressure sensor 46 which, in the example discussed below, is a pressure transducer that is arranged to sense pressure and pressure changes in the disposable tube 36.

The pressure sensor device 34 is in wired or wireless communication with a controller 50 on the ventilator 20. The controller 50 is shown schematically as "ventilator control electronic circuitry" in FIG. 2 and is arranged to control the supply of breathing gases to the patient, as well as actuation of the oxygen flush valve 51.

The pressure sensor device 34 may further include a speaker, which in the embodiment shown is an ear piece or ear bud 72. The ear bud 72 communicates with the ventilator to receive ventilator parameter information such as alarm information and/or ventilator status information and transmits the same to the caregiver 40.

It will be recognized by those skilled in the art that the present invention is not limited to the particular pressure sensor device 34 depicted and described herein. For example, the pressure sensor device 34 does not necessarily have to include a headset, and instead may include a neckband, earclip, or other retainer device for holding the transducer 46 in a position such that it is capable of sensing pressure changes resulting from breathing activity of the caregiver 40. The disposable tube 36 is also not essential and the invention does not necessarily require a disposable tube, as long as the pressure changes resulting from breathing activity of the caregiver 40 can be sensed by the transducer 46. It will also be recognized that the ear bud 72 is not essential, and if utilized, it may be replaced with different personal audio speaker components/arrangements or a video display, all of which are well known in the art.

Figure 2:
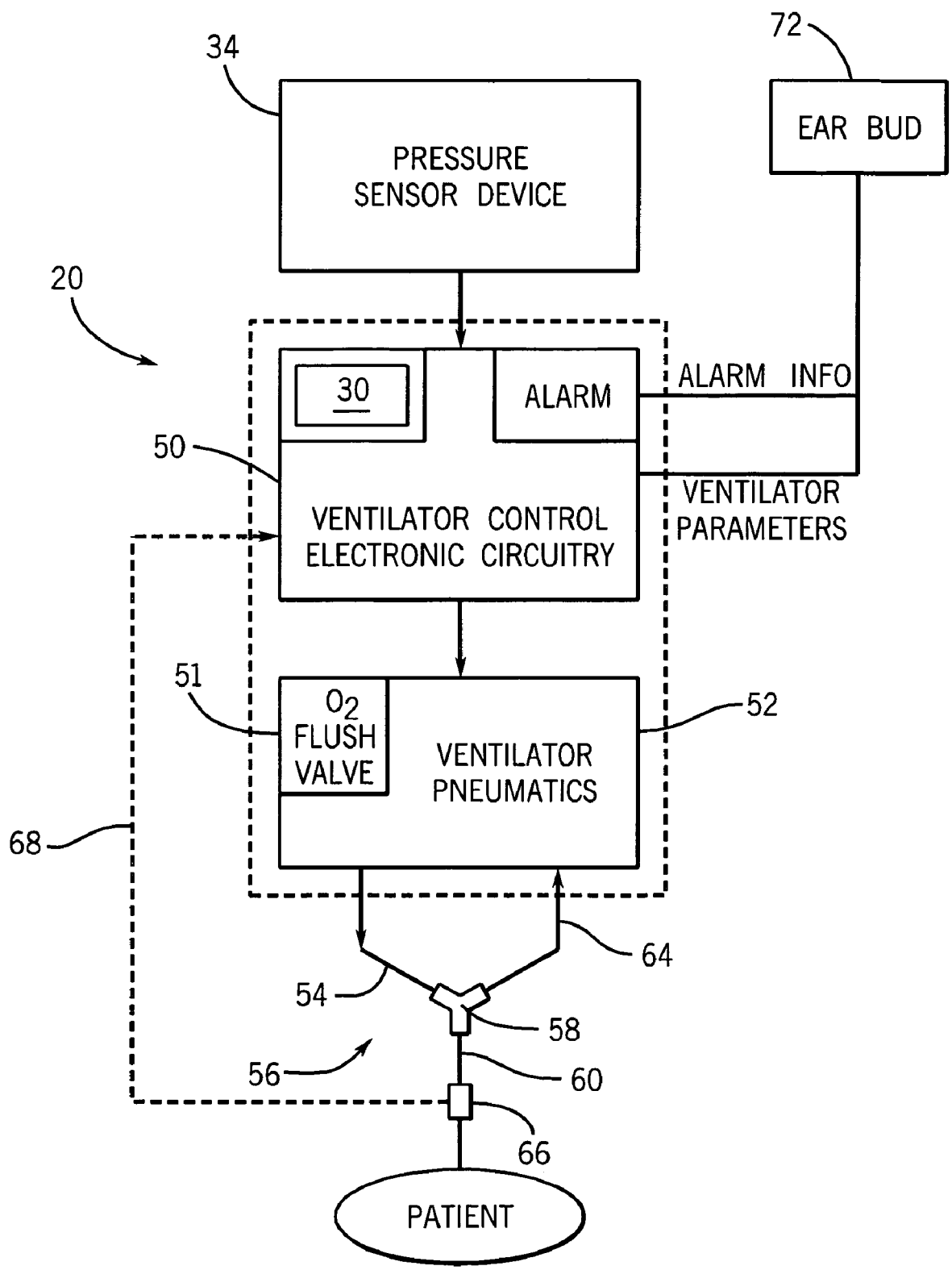
FIG. 2 is a schematic diagram of the arrangement of the present invention in conjunction with the ventilator apparatus.

FIG. 2 shows a schematic diagram of pressure sensor device 34 in conjunction with an apparatus 20 comprising a ventilator for a patient. Ventilator 20 includes electronic control circuitry or controller 50 that operates ventilator pneumatic circuitry 52. Pneumatic circuitry 52 comprises a source of pressurized gas that provides breathing gases to inspiratory limb 54 of a patient breathing circuit 56. Pneumatic circuitry 52 may provide breathing gases directly to the lungs of the patient, as in typical critical care application, or, a driving gas provided by pneumatic circuitry 52 may compress the bellows 29 containing the breathing gases which, in turn, supplies the gases to the patient, as in a typical anesthesia application. Pneumatic circuitry further comprises the oxygen flush valve 51 for providing a stream of oxygen to the breathing circuit.

The breathing gases pass through Y-connector 58 to a patient limb 60 for supply to the patient. The breathing gases are returned to the ventilator 20 in expiratory limb 64. In the embodiment shown in FIG. 2, pressure sensor 66 provides an airway pressure $P_{aw}$ signal in conductor 68 to ventilator control circuitry 50. The signal and conductor 68 is proportional to the pressure in patient limb 60 leading to the lungs of the patient. Ventilator control electronic circuitry 50 may include a monitor 30 that provides a numeric or graphic display of patient airway pressure $P_{aw}$, as well as other patient or apparatus parameters.

In operation, the pressure sensor device 34 communicates with the controller 50 on the ventilator 20 to control the delivery of respiratory support provided to a patient by the ventilator 20. The pressure sensor device 34 is arranged to sense changes in air pressure that correspond to breathing activity of the caregiver. For example, when the caregiver 40 closes his/her lips around the open end 42 of the tube 36 and forceably exhales, or "puffs", the pressure transducer 46 will sense an increase in air pressure in the disposable plastic tube 36. Conversely, when the caregiver 40 closes his/her lips around the open end 42 of the tube 36 and forceably inhales or "sips", the pressure transducer 46 will sense a decrease in air pressure in the disposable plastic tube 36. Based upon the sensed "puff" or "sip" the controller 50 thereafter controls at least one operational parameter of medical apparatus according to the following example of the method of the present invention.

Figure 3:
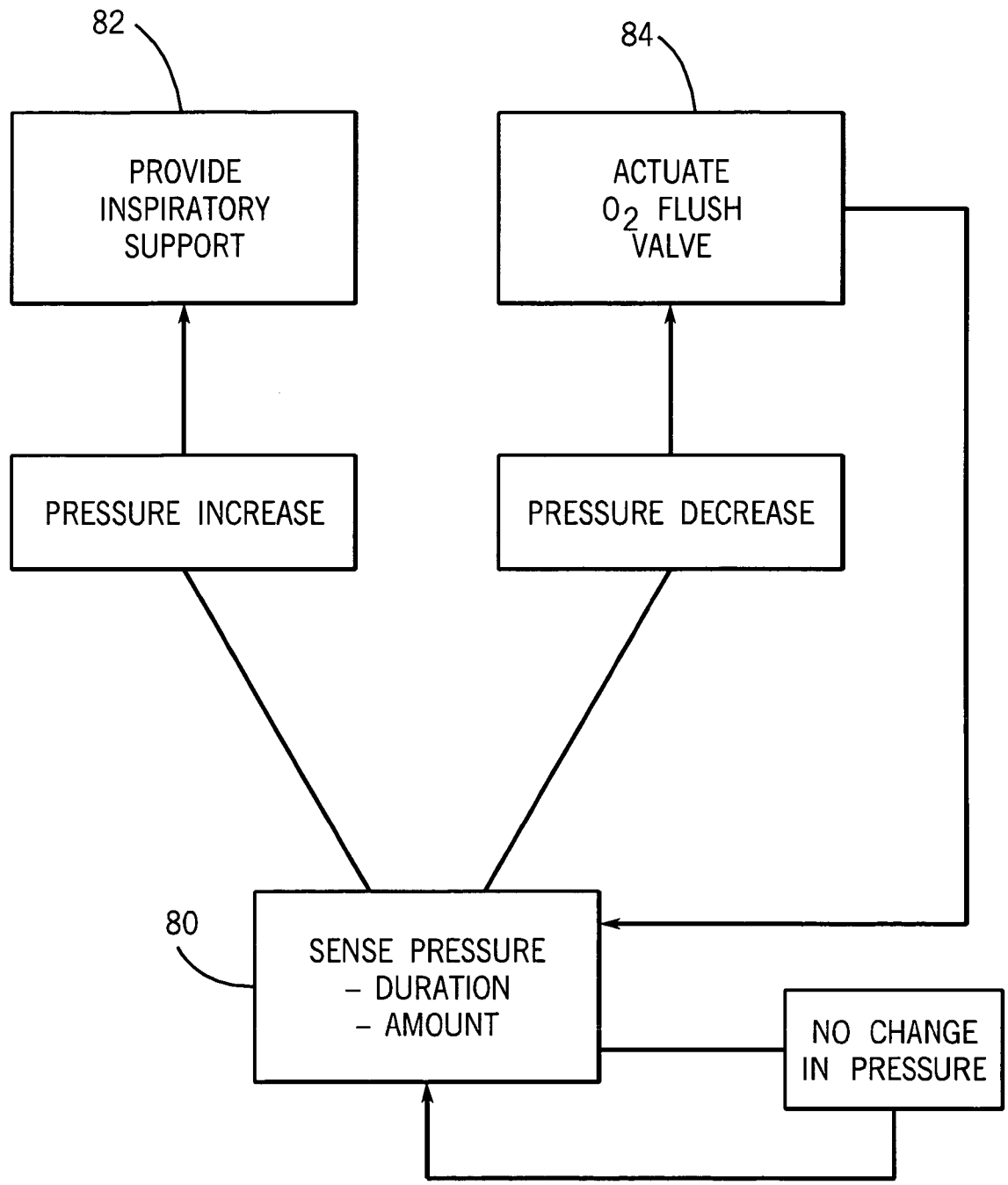
FIG. 3 is a flow chart depicting one embodiment of the steps of the method of the present invention.

Referring to FIG. 3, the pressure sensor device 34 periodically determines the air pressure within the plastic tube 36 at step 80. If there is no change in the air pressure, step 80 is periodically repeated, for example, at predetermined time intervals. If there is a pressure increase detected by the pressure transducer 46, the pressure increase is communicated to the controller 50 which subsequently controls the ventilator pneumatic circuitry 52 to provide inspiratory support to the patient at step 82. If, on the other hand, a pressure decrease is noted by the pressure transducer 46 at step 80, the decrease is communicated to the controller 50, which subsequently controls the ventilator pneumatic circuitry 52 to open the oxygen flush valve 51, at step 84.

In preferred arrangements, the pressure transducer 46 is sensitive to the amount of pressure change and the duration of pressure change, which relate to the strength and duration of breathing activity of the caregiver. As such, the pressure transducer is equipped to disregard the regular breathing activity of the caregiver 40 and only detect a forced "puff" or "sip" from the caregiver 40 that is intended to initiate a change in the ventilator control circuitry 50.

The pressure transducer 46 and controller 50 can also be arranged to control the operational characteristic of the medical apparatus based upon the duration and/or amount of pressure change in the tube 36. For example, the pressure transducer 46 can be arranged to sense the volume of pressure change in the tube 36 caused by a "puff" or "sip" from the caregiver 40. Based upon the amount of pressure change, the controller 50 can provide a certain volume of flow of breathing gases to the patient or a certain amount of oxygen from the oxygen flush. Similarly, the pressure transducer 46 can be arranged to sense the duration of the "puff" or "sip" from the caregiver 40 and provide breathing gases to the patient or oxygen from the oxygen flush for a corresponding duration.

With reference to FIG. 2, ventilator parameters and/or alarm information can be communicated to the caregiver 40 via the ear piece or ear bud 72. This further enhances the ability of the caregiver 40 to move about and be distant from the medical equipment and the patient. For example, if a break in the breathing circuit occurs and the level of breathing gas in the circuit decreases below a predetermined amount, an alarm signal can be sent to the pressure sensor device 34 and communicated to the caregiver 40 via the ear bud 72. Upon such notification, the caregiver 40 can "sip" on the disposable tube 36 to initiate the oxygen flush valve 51 and replenish the amount of oxygen in the breathing circuit.

According to the present invention, the caregiver is provided the ability to control the ventilator and to provide respiratory support without the need for manual control. Therefore, the caregiver advantageously has both hands available to perform other tasks. In addition, in the arrangement shown, the caregiver is free to move about and be distant from the patient and/or ventilator, which further adds to efficiency of care.

While this invention is susceptible to embodiments in many different forms, the drawings and specification describe in detail a preferred embodiment of the invention. They are not intended to limit the broad aspects of the invention to the embodiment illustrated.

What is claimed is:

1. A method of controlling at least one operational characteristic of medical equipment to provide medical care to a patient, the method comprising the steps of:
    sensing breathing activity of a caregiver; and
    controlling the medical equipment to provide medical care to a patient based upon the sensed breathing activity of the caregiver;
    wherein the step of sensing breathing activity of the care giver comprises the step of sensing a puff or a sip provided by the care giver to a pressure sensor device;
    wherein the medical equipment comprises a ventilator that is controlled based upon the sensed breathing activity.

2. The method of claim 1, wherein the ventilator is controlled to provide inspiratory support when a puff is detected and to actuate an oxygen flush valve when a sip is detected.

3. The method of claim 1, further comprising the step of controlling the operational parameter of the medical equipment based upon at least one of the duration of the breathing activity and the magnitude of the breathing activity.

4. A method of controlling at least one operational characteristics of medical equipment to provide medical care to a patient, the method comprising the steps of:
    controlling medical equipment based upon sensed breathing activity of a first person caregiver to provide medical care to a second person patient;
    wherein the step of sensing breathing activity of a caregiver comprises the step of sensing a puff or a sip provided by the caregiver to a pressure sensor device.

5. The method of claim 4, wherein the medical equipment comprises a ventilator that is controlled based upon the sensed breathing activity.

6. The method of claim 5, wherein the ventilator is controlled to provide inspiratory support when a puff is detected and to actuate an oxygen flush valve when a sip is detected.

7. The method of claim 4, further comprising the step of controlling the operational parameter of the medical equipment based upon at least one of the duration of the breathing activity and the magnitude of the breathing activity.

* * * * *